United States Patent [19]

Hoegerle

[11] 4,287,342
[45] Sep. 1, 1981

[54] 2,4,6-TRIHALO-5-ALKYL-AND 5-ALKENYLSULPHONYLPYRIMIDINES

[75] Inventor: Karl Hoegerle, Basel, Switzerland

[73] Assignee: Ciba-Geigy Corporation, Ardsley, N.Y.

[21] Appl. No.: 65,701

[22] Filed: Aug. 10, 1979

Related U.S. Application Data

[62] Division of Ser. No. 903,633, May 8, 1978, Pat. No. 4,188,483.

[30] Foreign Application Priority Data

May 9, 1977 [LU] Luxembourg .......................... 77288

[51] Int. Cl.³ ............................................ C07D 239/38
[52] U.S. Cl. ..................................... 544/298; 260/198
[58] Field of Search ......................................... 544/298

[56] References Cited

U.S. PATENT DOCUMENTS

| | | | |
|---|---|---|---|
| 3,120,507 | 2/1964 | Andrew et al. | 544/298 |
| 3,127,398 | 3/1964 | Bretschneider et al. | 544/302 |
| 3,682,916 | 8/1972 | Findeisen et al. | 544/334 |

FOREIGN PATENT DOCUMENTS

| | | |
|---|---|---|
| 1549494 | 11/1968 | France .................................... 544/298 |
| 1193290 | 5/1970 | United Kingdom . |
| 1378244 | 12/1974 | United Kingdom . |
| 1421923 | 1/1976 | United Kingdom . |

OTHER PUBLICATIONS

Carpenter et al., J. Chem. Soc., 1965, 3987–3990.

*Primary Examiner*—Paul M. Coughlan, Jr.
*Attorney, Agent, or Firm*—Michael W. Glynn

[57] ABSTRACT

There are described compounds of the formulae I and II

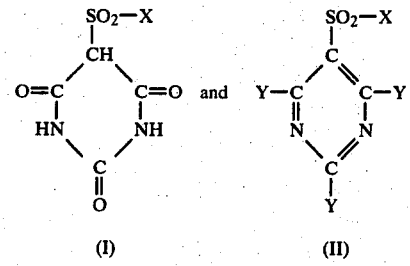

and also salts of compounds of the formula I, wherein X represents optionally substituted alkyl or alkenyl, and the Y's represent identical or different halogen atoms. The compounds of the formulae I and II are valuable intermediates which are suitable for producing, e.g., fibre-reactive dyes.

7 Claims, No Drawings

2,4,6-TRIHALO-5-ALKYL-AND 5-ALKENYLSULPHONYLPYRIMIDINES

This is a divisional of application Ser. No. 903,633 filed on May 8, 1978, U.S. Pat. No. 4,188,483.

The present invention relates to new 5-alkylsulphonyl- and 5-alkenylsulphonylbarbituric acids and to derivatives thereof, and also to processes for producing them. The new 5-alkylsulphonyl- and 5-alkenylsulphonylbarbituric acids and derivatives thereof are valuable intermediates for the production of dyes.

According to the German Offenlegungsschriften Nos. 1,670,854 and 1,770,774, differently substituted halopyrimidines can be produced by reaction of nitriles with isocyanide-dichlorides, preferably trichloromethyl-isocyanide-dichloride, optionally in the presence of catalysts, such as iron(III)chloride. The reaction temperatures are generally between about 200° and 350° C. The actual disclosure is limited to the production of 2,4,6-trichloropyrimidine, tetrachloropyrimidine, 2,4,6-trichloro-5-methyl-, -5-chloromethyl-, -5-phenyl-, -5-(4-nitrophenyl)-, -5-(3,4-dichlorophenyl)- and -5-(2,3,4-trichlorophenyl)-pyrimidine. In the German Offenlegungsschriften Nos. 2,113,298 and 2,208,972, which relate to specific reactive dyes, there is listed, among a large number of possible reactive components, also 2,4,6-trifluoro-5-methylsulphonylpyrimidine. The production thereof is however not described.

The present invention relates to new compounds of the formulae I and II

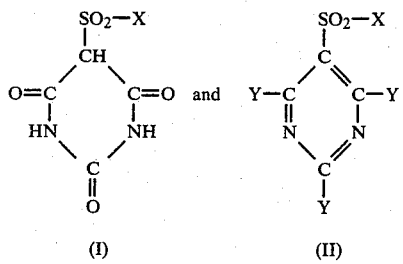

and also to salts of compounds of the formula I, wherein X represents optionally substituted alkyl or alkenyl, and the Y's represent identical or different halogen atoms.

The compounds of the formula I can exist in several tautomeric forms. In order to simplify the description, these compounds are represented in the formulae in only one of these tautomeric forms. It is expressly emphasised however that the specification, including the claims, relates always to compounds of the stated type in any one of these tautomeric forms.

Alkyl groups represented by X contain preferably 1–6 C atoms, particularly 1–4 C atoms, and may also be substituted, e.g. by one to three halogen atoms such as fluorine, chlorine or bromine, by an alkoxy group preferably having 1–6 C atoms and especially 1 or 2 C atoms, a phenyl group or a naphthyl group.

If X represents an alkenyl group, this advantageously has 2–4 C atoms.

Alkyl or alkenyl groups represented by X, as well as alkoxy substituents on alkyl groups X, can be straight-chain or branched-chain.

Examples of suitable groups X which may be mentioned are: the methyl, ethyl, n-propyl, isopropyl, n-butyl, isobutyl, sec-butyl, tert-butyl, n-hexyl, chloromethyl, trifluoromethyl group, alkoxymethyl groups having 1–6 C atoms in the alkoxy moiety, such as the methoxymethyl, ethoxymethyl, isopropoxymethyl and the n-butoxymethyl group, the methoxyethyl, β-ethoxyethyl, β-n-propoxyethyl, γ-ethoxypropyl, benzyl, β-phenylethyl, vinyl and allyl groups.

The compounds of the formula I can also be in the form of salts, such as salts with inorganic or organic bases, for example in the form of alkali metal salts or alkaline-earth metal salts, ammonium salts, trialkylammonium salts having 3–24 C atoms, particularly 3–12 C atoms, quaternary ammonium salts or salts with heterocyclic nitrogen compounds. Examples of such salts are the sodium, potassium, calcium, magnesium, $NH_4$-, trimethylammonium, triethylammonium, methyldiethylammonium, tri-n-octylammonium, benzyltrimethylammonium, tetramethylammonium and pyridinium salts. Preferred salts are trialkylammonium salts having 3–12 C atoms, especially triethylammonium salts, pyridinium salts, ammonium salts and in particular alkali metal salts, especially potassium salts and sodium salts.

The Y's can represent identical or different halogen atoms, such as chlorine, fluorine or bromine. Preferably, the Y's represent identical halogen atoms, especially fluorine atoms and more especially chlorine atoms.

Preferred are compounds of the formula I and salts thereof and also compounds of the formula II wherein X represents alkyl having 1–4 C atoms, which can be substituted by 1 to 3 halogen atoms, particularly chlorine atoms, an alkoxy group having 1 or 2 C atoms or a phenyl group, and the Y's each represent identical halogen atoms, especially fluorine and in particular chlorine atoms. Very particularly preferred compounds of the formula I, salts thereof and compounds of the formula II are those wherein X represents methyl, and the Y's each represent fluorine or chlorine.

The following may be mentioned as specific representatives of compounds of the formulae I and II:
5-methylsulphonylbarbituric acid, 5-ethylsulphonyl-, 5-isopropylsulphonyl-, 5-n-butylsulphonyl-, 5-chloromethylsulphonyl-, 5-dichloromethylsulphonyl-, 5-trifluoromethylsulphonyl-, 5-ethoxymethylsulphonyl-, 5-β-ethoxyethylsulphonyl-, 5-isopropoxymethylsulphonyl-, 5-benzylsulphonyl-, 5-β-phenylethylsulphonyl or 5-allylsulphonylbarbituric acid and salts thereof; 5-methylsulphonyl-2,4,6-trichloro-, -2,4,6-tribromo- and -2,4,6-trifluoropyrimidine, 5-ethylsulphonyl-2,4,6-trichloropyrimidine, 5-isopropylsulphonyl-2,4,6-trichloropyrimidine, 5-n-butylsulphonyl-2,4,6-trichloropyrimidine, 5-chloromethylsulphonyl-2,4,6-trichloropyrimidine, 5-dichloromethylsulphonyl-2,4,6-trichloropyrimidine, 5-trifluoromethylsulphonyl-2,4,6-trichloropyrimidine, 5-ethoxymethylsulphonyl-2,4,6-trichloropyrimidine, 5-isopropoxymethylsulphonyl-2,4,6-tribromopyrimidine, 5-allylsulphonyl-2,4,6-trichloropyrimidine, 5-benzylsulphonyl-2,4,6-trichloro-, -2,4,6-tribromo- and -2,4,6-trifluoropyrimidine and 5-β-phenylethylsulphonyl-2,4,6-trichloropyrimidine.

The compounds of the formula I and salts thereof can be produced by reacting a barbituric acid salt with a compound of the formula III $$Z-SO_2-X \qquad (III)$$

wherein Z represents a halogen atom or $-O-SO_2-X$, and X has the meaning given under the formulae I and II.

If Z represents a halogen atom, it is for example fluorine or bromine, particularly however chlorine.

Suitable barbituric acid salts are, for example, salts with inorganic or organic bases of the aforementioned type, such as alkali metal salts or alkaline-earth metal salts, ammonium salts, trialkylammonium salts having 3-24 C atoms, and particularly 3-12 C atoms, quaternary ammonium salts or salts with heterocyclic nitrogen compounds. Those preferred are trialkylammonium salts having 3-12 C atoms, especially the triethylammonium salt, the pyridinium and ammonium salt and, in particular, alkali metal salts, especially the sodium and potassium salt.

The barbituric acid salts can be produced in a manner known per se either before addition to the reaction medium or in the reaction medium itself, i.e. in situ.

The following may be mentioned as suitable starting products of the formula III: methanesulphonyl chloride, methane sulphonyl bromide, chloromethanesulphonic acid chloride, bromomethanesulphonic acid bromide, trichloromethanesulphonic acid chloride, ethanesulphonic acid chloride, ethanesulphonic acid bromide, vinylsulphonic acid chloride, allylsulphonic acid chloride, 3-chloropropanesulphonic acid chloride, 1-chlorobutane-3-sulphonic acid chloride, benzylsulphonic acid chloride and β-phenylethylsulphonic acid chloride.

The reaction is advantageously performed in the presence of an inorganic or organic base. Suitable bases are for example: hydroxides, carbonates, hydrogen carbonates or acetates of alkali metals or alkaline-earth metals, or organic bases such as tertiary amines, e.g. trialkylamines, particularly triethylamine, or nitrogen-containing heterocyclic bases, such as pyridine.

The bases mentioned are used preferably in such amounts that the barbituric acid is always in the form of salt right up to the end of the reaction.

The reaction can be performed in an aqueous medium, in an inert organic solvent or in a mixture of various inert organic solvents, in a mixture of water and one or more inert organic solvents, and also in a solvent two-phase system.

Suitable inert organic solvents are, for example: N,N-dialkylamides of aliphatic monocarboxylic acids having 1-3 C atoms in the acid moiety, such as N,N-dimethylformamide, N,N-dimethylacetamide or N,N-diethylacetamide; aliphatic and cycloaliphatic ketones, such as acetone, methyl ethyl ketone, cyclopentanone and cyclohexanone; cyclic amides such as N-methyl-2-pyrrolidone, N-acetyl-2-pyrrolidone or N-methyl-$\epsilon$-caprolactam; aliphatic monocarboxylic acids having 1-4 C atoms, such as acetic acid and propionic acid; dialkyl sulphoxides such as dimethyl sulphoxide and diethyl sulphoxide; and pyridine.

Suitable solvent two-phase systems are, in particular, water/organic solvent systems, such as water/methylene chloride or water/toluene.

The reaction in aqueous medium with a pH value of between about 8 and 14, preferably between 9 and 12, is preferred, with the barbituric acid salt being generally formed in situ.

According to a particularly preferred embodiment, the reaction is performed in a strongly alkaline aqueous solution (pH between 9 and 12), the base used being especially sodium hydroxide or potassium hydroxide.

For the reaction in organic or aqueous/organic medium, the bases advantageously used are tertiary amines such as trialkylamines, e.g. triethylamine, or nitrogen-containing heterocyclic bases such as pyridine, or alkali metal acetates, for example sodium acetate.

The reaction of the barbituric acid salts with the compounds of the formula III is advantageously performed at temperatures between $-20°$ C. and $+100°$ C., preferably at a temperature of between $+10°$ and $+50°$ C.

After completion of the reaction, the strongly acid barbituric acid derivatives of the formula I precipitate, either directly or on acidification of the reaction solution, e.g. with concentrated hydrochloric acid or concentrated sulphuric acid, in the form of salts. For purification, these can be recrystallised from water. It is possible to obtain from the salts if desired, in a manner known per se, the free 5-alkylsulphonyl- or 5-alkenylsulphonylbarbituric acids, for example by treating the salts with synthetic resins containing strongly acid ion exchangers, such as $SO_3^{\ominus}$ groups. Alternatively, it is also possible to convert in a manner known per se the barbituric acid derivatives of the formula I into salts of the aforementioned type, or to convert the salts obtained from the reaction into other salts.

The compounds of the formula II can be obtained by treating a compound of the formula I, or salts thereof, with a halogenating agent, and subjecting the resulting 5-alkylsulphonyl- or 5-alkenylsulphonylhalopyrimidine optionally to a halogen-exchange reaction.

Suitable halogenating agents are, for example, phosphorus(V) oxyhalides, such as phosphorus(V)oxychloride, -bromide and -fluoride, methylphosphorus(V)oxydichloride ($CH_3POCl_2$), phenylphosphorus(V)oxydichloride ($C_6H_5POCl_2$), phosgene, thionyl bromide, thionyl chloride and $SF_4$.

It is also possible to use mixtures of various halogenating agents, for example mixtures of phosphorus(V)oxychloride and phosphorus(V)oxybromide, or alternatively halogenating agents having different halogen atoms, e.g. so-called mixed thionyl halides, such as SOClF or SOBrCl. There are then obtained compounds of the formula II wherein the three Y's represent different halogen atoms.

Halogenating agents having identical halogen atoms are preferably used, particularly chlorinating agents, such as chlorine-phosphorus compounds, especially phosphorus(V)-oxychloride.

It is generally advantageous to perform the reaction in the presence of a catalyst. Compounds acting as catalysts are, for example, aliphatic or aromatic tertiary bases, such as N,N-dimethylaniline, N,N-diethylaniline, N,N-dimethylformamide and N,N-dimethylacetamide.

The catalysts are in general used in an amount of 1-200 mol %, relative to the employed amount of the compound of the formula I or of the salt thereof. Equimolar amounts of catalyst are preferably used.

The reaction of the compounds of the formula I, or of salts thereof, with the halogenating agent is preferably performed in an inert organic solvent. Suitable for this purpose are, for example, aromatic hydrocarbons such as xylene, toluene, chlorobenzene or nitrobenzene; and also chlorinated aliphatic or cycloaliphatic hydrocarbons such as trichloroethylene, carbon tetrachloride and cyclohexyl chloride.

Also excess halogenating agent, particularly phosphorus(V) oxychloride, can serve as solvent.

Halogenation is advantageously performed at a temperature of between 20° and 250° C., preferably at a temperature of between 50° and 130° C.

Compounds of the formula II wherein one or two Y's represent chlorine atoms, and the remaining Y's bromine or fluorine atoms, or wherein all three Y's represent bromine or fluorine atoms, can also be produced by reacting compounds of the formula II obtained according to the invention, wherein all three Y's represent chlorine atoms, with a brominating or fluorinating agent, such as phosphorus tribromide, anhydrous hydrogen fluoride, alkali metal fluorides or potassium fluorosulphinate, until one, two or all three chlorine atoms are substituted by bromine or fluorine atoms.

Thus, for example, the compounds of the formula II wherein all three Y's represent chlorine, and X has the given meaning, can be converted into the bromine or fluorine analogues by converting 5-alkylsulphonyl- or 5-alkenylsulphonyl-2,4,6-trichloropyrimidines of the formula II, for example 5-methylsulphonyl-2,4,6-trichloropyrimidine, by reaction with phosphorus tribromide, which may also serve as solvent, into the corresponding 2,4,6-tribromopyrimidine; or by converting compounds of the formula II wherein each Y represents chlorine, by reaction with anhydrous hydrogen fluoride, with potassium fluorosulphinate, or with an alkali metal fluoride undiluted or in the presence of a high-boiling aprotic organic solvent, into the corresponding 2,4,6-trifluoro compound. Suitable solvents for this halogen-exchange reaction are, for example, aromatic hydrocarbons, such as toluene and xylenes; N.N-dialkylamides of aliphatic monocarboxylic acids of the aforementioned type, such as N,N-dimethylformamide and N,N-dimethylacetamide; dialkylsulphoxides, particularly dimethylsulphoxide; cyclic ethers and cyclic amides, such as tetrahydrofuran, tetrahydropyrane, N-methyl-2-pyrrolidone and N-acetyl-2-pyrrolidone; hexamethylphosphoric acid triamide (hexametapol); and N,N,N',N'-tetramethylurea or tetrahydrothiophene dioxide (sulpholane).

The reaction temperatures for the halogen-exchange reaction are advantageously between 20° and 250° C., preferably between 50° and 130° C.

The compounds of the formula I, salts thereof and the compounds of the formula II can be produced by the process according to the invention under mild reaction conditions and in good to very good yields.

The compounds of the formulae I and II are valuable intermediates which are suitable, for example, for producing dyes. By condensation of compounds of the formula II, which for their part are produced, as described in the foregoing, from the compounds of the formula I or from salts thereof, particularly compounds of the formula II wherein X and Y have the aforementioned preferred meaning, with dyes containing amino groups, there are obtained fibre-reactive dyes which give on cellulose fibres dyeings fast to washing and to light and which are distinguished by high reactivity and good fastness to acids.

EXAMPLE 1

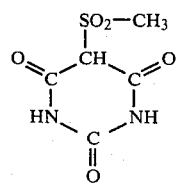

(a) 12.8 g (0.1 mol) of anhydrous barbituric acid is dissolved in a mixture of 250 ml of water and 20 ml of 10 N sodium hydroxide solution at room temperature (20°–25° C.). The solution is cooled to 5° to 10° C.; to the clear solution is added dropwise, in the course of 40 minutes, 17.1 g (0.15 mol) of methanesulphonyl chloride, during which time the pH value of the solution is kept at 12 by the addition of 2 N sodium hydroxide solution. The reaction mixture, which forms a pale suspension, is allowed to warm up to room temperature, and is then left to stand for 15 to 20 hours. The pH value is subsequently adjusted to 1 by the addition of 10 ml of concentrated hydrochloric acid; the reaction mixture is then cooled to 5° C. and filtered; the precipitate is washed with a small amount of cold water, and dried in vacuo at 60°;

yield: 21.5 g (94%) of the sodium salt of 5-methylsulphonylbarbituric acid;

melting point: 346°–347° C. (decomposition).

(b) Production of the free 5-methylsulphonylbarbituric acid from the sodium salt thereof On a column, 10 g of a strongly acid, moist ion exchanger ("Amberlite IR 120," a synthetic resin containing $SO_3^\ominus$ groups) is washed with de-ionised water until the washing water flows off clear, colourless and with a pH value of 7. 250 g of the sodium salt of 5-methylsulphonylbarbituric acid, dissolved in a small amount of warm water (30°–40° C.), is then placed onto the column and subsequently washed with water until the eluate again has a pH value of 7. The aqueous solution is evaporated to dryness in vacuo at about 30° C. to yield colourless crystals; m.p. 262° C., with decomposition. If there should still be traces of the sodium salt in the product (indicated by yellow flame colouration), these traces can be removed by extraction of the free compound from the sodium salt with acetone.

EXAMPLES 2–7

The following compounds of the formula I are obtained in a manner analogous to that described in Example 1 by using, instead of 17.1 g of methanesulphonyl chloride, equivalent amounts of ethanesulphonic acid chloride, n-butanesulphonyl chloride, chloromethanesulphonyl chloride, dichloromethanesulphonyl chloride, β-ethoxyethanesulphonyl chloride and benzylsulphonyl chloride, respectively:

the sodium salt of 5-ethylsulphonylbarbituric acid, m.p. >360° C.; (decomposition, yield 86% of theory);
the sodium salt of 5-n-butylsulphonylbarbituric acid, m.p. >360° C. (decomposition, yield 97% of theory);
the sodium salt of 5-chloromethylsulphonylbarbituric acid, m.p. >360° C. (decomposition, yield 56% of theory);
the sodium salt of 5-dichloromethylsulphonylbarbituric acid, m.p. >360° C. (decomposition, yield 20% of theory);
the sodium salt of 5-β-ethoxyethylsulphonylbarbituric acid, m.p. >360° C. (decomposition, yield 65% of theory); and
the sodium salt of 5-benzylsulphonylbarbituric acid, m.p. >360° C. (decomposition, yield 40% of theory).

EXAMPLE 8

A solution of 25 g (1.43 mols) of 96% methanesulphonic acid anhydride in 25 ml of acetone is added dropwise to a solution of 11.9 g (0.09 mol) of barbituric acid in 200 ml of water and 18 ml of 10 N sodium hydroxide solution at room temperature. The pH value is maintained at 11.5-12 by the addition of 30 ml of 5 N sodium hydroxide solution. The reaction is complete (pH constant) after 4 hours' stirring of the reaction mixture at room temperature. To the suspension obtained is added 20 ml of concentrated hydrochloric acid (pH 1), and the precipitate which separates out is filtered off to give 17.7 g of the sodium salt of 5-methylsulphonylbarbituric acid (86% of theory).

EXAMPLE 9

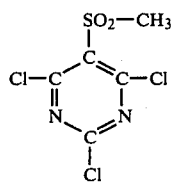

12.5 ml (0.1 mol) of N,N-dimethylaniline is slowly added at room temperature to 100 ml of phosphorus(V)oxychloride. To this solution is added at room temperature 22.8 g (0.1 mol) of the compound obtained according to Example 1 (sodium salt, or a corresponding amount of the free acid). The reaction mixture is heated, and at about 55° C. the evolution of hydrogen chloride slowly commences. The suspension is left boiling under reflux for 15 to 20 hours; the cloudy solution is subsequently poured onto water at 25° to 28° C., and the whole is stirred for 20 minutes. The precipitate which has formed (17.6 g) is air-dried and then taken up in methylene chloride; the solution obtained is treated with charcoal and sodium sulphate; it is filtered till clear, and the filtrate is concentrated to dryness in a rotary evaporator to yield 17.3 g of solid substance. This is dissolved in 100 ml of toluene and treated in solution with active charcoal; it is subsequently filtered till clear, cooled and allowed to crystallise out. From several crystal fractions is finally obtained about 15.8 g (~60.4% of theory) of a product of which the main fraction has a melting point of 146°-147° C.

EXAMPLES 10-15

If the procedure as described in Example 9 is followed with the exception that instead of using 22.8 g of the sodium salt of 5-methylsulphonylbarbituric acid there are used equivalent amounts of
the sodium salt of 5-ethylsulphonylbarbituric acid,
the sodium salt of 5-n-butylsulphonylbarbituric acid,
the sodium salt of 5-chloromethylsulphonylbarbituric acid,
the sodium salt of 5-dichloromethylsulphonylbarbituric acid,
the sodium salt of 5-β-ethoxyethylsulphonylbarbituric acid, and
the sodium salt of 5-benzylsulphonylbarbituric acid,
there are obtained respectively the following compounds:
5-ethylsulphonyl-2,4,6-trichloropyrimidine, m.p. 135°-136° C., yield 70% of theory;
5-n-butylsulphonyl-2,4,6-trichloropyrimidine, m.p. 71°-72° C., yield 54% of theory,
5-chloromethylsulphonyl-2,4,6-trichloropyrimidine, m.p. 152°-153° C., yield 69% of theory,
5-dichloromethylsulphonyl-2,4,6-trichloropyrimidine, m.p. 150°-152° C.,
5-β-ethoxyethylsulphonyl-2,4,6-trichloropyrimidine, m.p. 133°-134° C., yield 42% of theory, and
5-benzylsulphonyl-2,4,6-trichloropyrimidine, m.p. 160°-162° C., yield 60% of theory.

EXAMPLE 16

A solution of 2.6 g (0.01 mol) of 5-methylsulphonyl-2,4,6-trichloropyrimidine, obtained according to Example 9, in 75 ml of phosphorus tribromide is kept for 24 hours at an internal temperature of 115°-120° C. The phosphorus tribromide is subsequently distilled off in a rotary evaporator, and the solid residue is suspended in methylene chloride or benzene and then filtered off. From benzene crystallises 5-methylsulphonyl-2,4,6-tribromopyrimidine in the form of colourless crystals, m.p. 206°-208° C.; yield 2.7 g=68% of theory.

EXAMPLE 17

A suspension of 78.5 g (0.3 mol) of 5-methylsulphonyl-2,4,6-trichloropyrimidine and 240 g of 90% potassium fluorosulphinate in 1250 ml of anhydrous xylene is slowly heated. The evolution of $SO_2$ commences at 93° C. and has virtually ceased after a refluxing time of two hours. The reaction is completed by 18 hours of refluxing. The light-brown suspension obtained is clarified at 70° C. with animal charcoal, and the solvent is distilled off, at 40° C. bath temperature, in a rotary evaporator. The residue is distilled in high vacuum at 118°-125° C./0.03 Torr. There is thus obtained 48 g of 5-methylsulphonyl-2,4,6-trifluoropyrimidine, m.p. 103°-105° C. (yield 75% of theory).

EXAMPLE 18

8.76 g of the dye of the formula

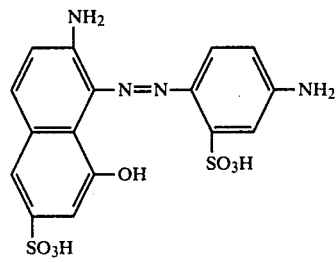

is dissolved neutral in 300 parts of water, and 6.68 g of sodium acetate is added. To this solution is added at room temperature, with vigorous stirring, a solution of 5.75 g of 5-methylsulphonyl-2,4,6-trichloropyrimidine in 30 ml of acetone. After complete acylation, the solution is filtered until clear. The reactive dye obtained is salted out with potassium chloride, filtered off, and dried in vacuo at about 50° C.

The dye thus obtained dyes cotton in the exhaust process in bluish-red shades.

I claim:
1. A compound of the formula II

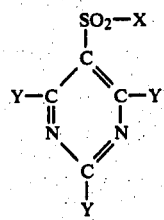

wherein
X represents alkenyl having 2 to 4 carbon atoms or alkyl of 1 to 6 carbon atoms which is unsubstituted or is substituted by substituents selected from the group consisting of 1 to 3 halogen, alkoxy having 1-6 carbon atoms, phenyl and naphthyl, and each Y represents an identical or different halogen.

2. A compound according to claim 1, wherein each Y is identical.

3. A compound according to claim 1, wherein X represents alkyl of 1 to 4 carbon atoms, which is unsubstituted or is substituted by 1 to 3 chloro, alkoxy of 1 to 2 carbon atoms or phenyl; and each Y is an identical halogen.

4. A compound according to claim 1, wherein X represents methyl and each Y is fluoro or chloro.

5. A compound according to claim 1, wherein each Y is chloro.

6. A compound as claimed in claim 1 which is the 5-methylsulfonyl-2,4,6-trichloropyrimidine.

7. A compound as claimed in claim 1 which is the 5-methylsulfonyl-2,4,6-trifluoropyrimidine.

* * * * *